(12) United States Patent
Weber et al.

(10) Patent No.: US 10,436,966 B2
(45) Date of Patent: Oct. 8, 2019

(54) ILLUMINATING DEVICE

(71) Applicant: Richard Wolf GmbH, Knittlingen (DE)

(72) Inventors: Bernd Claus Weber, Karlsruhe (DE); Moritz Tewes, Bretten (DE); Marco Hoffmann, Waghäusel (DE); Dieter Götz, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 16/072,339

(22) PCT Filed: Jan. 25, 2017

(86) PCT No.: PCT/DE2017/200007
§ 371 (c)(1),
(2) Date: Jul. 24, 2018

(87) PCT Pub. No.: WO2017/129186
PCT Pub. Date: Aug. 3, 2017

(65) Prior Publication Data
US 2019/0033506 A1    Jan. 31, 2019

(30) Foreign Application Priority Data
Jan. 29, 2016  (DE) .................. 10 2016 201 324

(51) Int. Cl.
*F21V 8/00*         (2006.01)
*A61B 1/06*         (2006.01)
(Continued)

(52) U.S. Cl.
CPC ........ *G02B 6/0006* (2013.01); *A61B 1/00167* (2013.01); *A61B 1/0669* (2013.01);
(Continued)

(58) Field of Classification Search
CPC .... G02B 6/0006; G02B 6/262; G02B 6/4298; G02B 6/04; G02B 6/42; G02B 6/26;
(Continued)

(56) References Cited

U.S. PATENT DOCUMENTS 3,779,628 A   12/1973  Kapron et al.
3,832,028 A    8/1974  Kapron
(Continued)

FOREIGN PATENT DOCUMENTS

DE    10 2005 018336 A1    8/2006
EP         0 083 527 A1    7/1983
(Continued)

*Primary Examiner* — Thomas M Sember
(74) *Attorney, Agent, or Firm* — McGlew and Tuttle, P.C.

(57) ABSTRACT

An illumination device is provided with an LED (2) as a light source and with a fiber-optic (6) for leading further the light which is emitted by the LED (2). A light transmission part (10) is arranged between the LED (2) and the fiber-optic (6). This light transmission part (10) includes two sections (14, 16), of which a first section (14) directly faces the LED (2) and includes a cross section which widens with an increasing distance to the LED (2) as well includes a lateral surface (22) which in an angularly independent manner reflects the radiation which enters into the first section (14) and a second section (16) directly faces the fiber optic (6) and includes at least one lateral surface (24) which in an angularly dependent manner reflects radiation which enters from the first section (14) into the second section (16).

20 Claims, 4 Drawing Sheets

(51) Int. Cl.
*A61B 1/07* (2006.01)
*G02B 6/42* (2006.01)
*G02B 6/26* (2006.01)
*G02B 23/24* (2006.01)
*A61B 1/00* (2006.01)
*G02B 6/04* (2006.01)

(52) U.S. Cl.
CPC .............. *A61B 1/0684* (2013.01); *A61B 1/07* (2013.01); *G02B 6/26* (2013.01); *G02B 6/262* (2013.01); *G02B 6/42* (2013.01); *G02B 6/04* (2013.01); *G02B 23/2469* (2013.01)

(58) Field of Classification Search
CPC . A61B 1/00167; A61B 1/0669; A61B 1/0684; A61B 1/07
See application file for complete search history.

(56) References Cited

U.S. PATENT DOCUMENTS

| | | |
|---|---|---|
| 2005/0046807 A1 | 3/2005 | Hanano |
| 2006/0263015 A1 | 11/2006 | Fincato et al. |
| 2010/0176311 A1 | 7/2010 | Segi et al. |
| 2013/0329433 A1 | 12/2013 | Lin et al. |

FOREIGN PATENT DOCUMENTS

| | | | |
|---|---|---|---|
| EP | 0083527 A1 * | 7/1983 | ............ G02B 6/262 |
| EP | 0224282 A1 | 6/1987 | |
| EP | 1 491 815 A2 | 12/2004 | |
| GB | 2169096 A | 7/1986 | |

\* cited by examiner

ILLUMINATING DEVICE

CROSS REFERENCE TO RELATED APPLICATIONS

This application is a United States National Phase Application of International Application PCT/DE2017/200007, filed Jan. 25, 2017, and claims the benefit of priority under 35 U.S.C. § 119 of German Application 10 2016 201 324.6, filed Jan. 29, 2016, the entire contents of which are incorporated herein by reference.

FIELD OF THE INVENTION

The present invention relates to an illumination device with an LED, with a fiber-optic and with a light transmission part which is arranged between the LED and the fibre-optic.

BACKGROUND OF THE INVENTION

Those illumination devices, concerning which an LED is applied in combination with a fiber-optic, in order to transport the light which is emitted by the LED to a location which is remote from the LED form the basis of the invention. Such illumination devices nowadays have a significant role to play in different technical fields. In this context for example, endoscopes are known, concerning which, for illumination purposes, light must be provided at the distal end of an elongate shank, wherein the LED is arranged at the proximal side of the shank either as a part of the endoscope or as part of a separate light source which is connectable to the endoscope.

If a large light yield is necessary at the end which is away from the LED, then accordingly large light fluxes must already be provided by the LED and coupled into the fiber optic. At the location of the coupling of light into the fiber-optic, this leads to a comparatively high thermal loading which can be explained by the fact that also those light beams which are emitted by the LED and have a comparatively large angle to the optical axis of the fiber-optic or to the optical axis of its fibers also reach the fiber-optic and due to the comparatively small numeric aperture of the fiber-optic or its fibers cannot be transmitted through the fiber-optic and instead of this are absorbed and converted into heat. In the most unfavorable case, this thermal loading can lead to a damaging of the fiber-optic.

SUMMARY OF THE INVENTION

It is the object of the invention to provide an illumination device of the previously described type which provides high light fluxes at the exit side of the fiber-optic, wherein the thermal loading of the fiber-optic in the region of the coupling of the light emitted by the LED into the fiber-optic is to be as low as possible.

The illumination device according to the invention is provided with an LED as a light source and with a fiber-optic for leading further the light which is emitted by the LED. The fiber-optic is typically arranged in front of a light-emitting surface of the LED, which is to say is typically arranged in front of the LED in the main propagation direction of the light which is emitted by the LED. The fiber-optic can be a single rod of a core-cladding glass or also a fiber bundle whose fibers are each formed from a core-cladding glass. A core-cladding glass here is to be understood in the conventional context as a glass body which consists of at least two glass types, with regard to which a core of first glass type, the core glass, is surrounded by a cladding of at least one other glass type, the cladding glass. A light transmission part is arranged between the LED and the fiber-optic. This light transmission part which is transparent to the light beams which are emitted by the LED serves for the targeted coupling of the light beams which are emitted by the LED, into the fiber-optic.

The illumination device according to the invention is characterized in that the light transmission part comprises two sections, of which a first section directly faces the LED and comprises a cross section which widens with an increasing distance to the LED and further comprises a lateral surface which in an angularly independent manner reflects the radiation which enters the first section, and a second section directly faces the fiber-optic and comprises at least one lateral surface which in an angularly dependent manner reflects the radiation which enters from the first section into the second section. Herein, it is not the complete lateral surface of the first section which necessarily needs to be reflective in an angularly independent manner to the radiation which enters into this, and the complete lateral surface of the second section does not necessarily have to be reflecting in an angularly dependent manner to the radiation which enters from the first section into the second section. However, the case in which the complete lateral surface of the first section is reflective in an annularly independent manner to the radiation which enters into this, without herein being restricted to this special case, and in which the complete lateral surface of the second section is reflective in an angularly dependent manner to the radiation which enters from the first section into the second section, wherein here too there is no restriction to this special case, is always considered with a view to a simplified description and explanation.

The first section of the light transmission part which directly faces the LED, at its end which is away from the LED usefully has a cross section which roughly corresponds to the cross section of the fiber-optic. Compared to this cross section, the cross section of the first section is significantly smaller at its end which faces the LED. Hereby, when dimensioning this cross section, one is however to ensure that the light transmission part, at the end which faces the LED, can receive a maximum of the light beams which are emitted by the LED.

A part of these light beams which enter into the first section of the light transmission part has a comparatively large angle to the middle axis of the light transmission part and is therefore incident upon the lateral surface which delimits the first section of the light transmission part at the outer periphery. On account of the characteristic of this lateral surface, of reflecting the light beams in an angularly independent manner, none of the light beams which are incident upon the lateral surface are lost at the lateral surface, but instead all these light beams are transmitted further to the second section of the light transmission part by way of reflection. Herein, the shaping of the first section of the light transmission part with the cross section which continuously enlarges in the direction of the second section of the light transmission part has the effect that the light beam which are reflected by the lateral surface have an angle relative to the middle axis of the light transmission part which is smaller than that which they had on entering into the first section of the light transmission part. The share of the light beams which are emitted by the LED and which can be transmitted in the fiber-optic which is subsequent to the light transmission part on account of its comparatively low numeric aperture or on account of the low numeric aperture of the fibers which are applied there is increased byway of this angular transformation which is effected in the first section of the light transmission part on its lateral surface. Hereby, the quotient of the light entry surface and the light exit surface of the first section, indicated as the aspect ratio, is decisive, since a minimal aspect ratio effects a maximal angular transformation. However, a minimisation of the aspect ratio is restricted due to the fact that, as already noted, on dimensioning the cross section at the end of the first section which faces the LED, one is to take account of the fact that the light transmission part, at the end which faces the LED, is to receive a maximum of the light means emitted by the LED and the cross section at the end which is away from the LED is to correspond roughly to the cross section of the fiber-optic. However, despite this restriction, light fluxes which are significantly greater than the case with comparable illumination devices of the state of the art are achieved at the exit side of the fiber-optic with the illumination device according to the invention.

Irrespective of the angular transformation which takes place in the first section of the light transmission part, a few light beams with such a large angle with respect to the middle axis of the light transmission part that these light beam cannot be transmitted up to the end of the fiber-optic which is away from the light transmission part on account of the comparatively low numeric aperture of the fiber-optic or on account of the low numeric aperture of the individual fibers of the fiber-optic can still be present at the exit side of the first section in dependence on the selected aspect ratio. Since these light beams are of no significance with regard to the light yield at the end of the fiber-optic which is away from the light transmission part and these light beams even cause a thermal loading of the fiber-optic and could therefore lead to a damage to the fiber-optic, the task of the second section of the light transmission part which preferably has a constant cross section over the its complete length in the direction of the middle axis of the light transmission part and is therefore designed in a rod like manner is to eliminate these light beams. For this purpose, the second section of the light transmission part comprises at least one lateral surface, at which only those light beams which are incident thereon are reflected, which can be transmitted by the fiber-optic on account of the restricted numerical aperture of the fiber-optic or of the restricted numeric aperture of the fibers of the fiber-optic, whereas light beams which have a large angle relative to the middle axis of the light transmission part and cannot be transmitted by the fiber-optic already leave the second section of the light transmission part at the location, at which they are incident upon the lateral surface.

Generally, the light transmission part should be arranged as close as possible to the LED, so that a as large as possible part of the light which is emitted by the LED can get into the first section of the light transmission part. However, it is also advantageous if a medium which has a refractive index which is smaller than the refractive index of the material, from which the first section of the light transmission part is formed, is located between the LED and the light transmission part, so that the light beams which are emitted by the LED are refracted as greatly as possible in the direction of the middle axis of the light transmission part on entry into the first section of the light transmission part. Inasmuch as this is concerned, according to an advantageous further development of the invention, one envisages the light transmission part being arranged distanced to the LED and an intermediate space between the LED and the light transmission part being filled with gas. Herein, the distance between the LED and the light transmission part should usefully be kept as small as possible in view of the light yield of the light transmission part. The then comparatively narrow intermediate space between the LED and the light transmission part is advantageously filled with air or another gas whose refractive index is roughly n=1. Since the first section of the light transmission part is preferably of glass, crystal or a plastic which is transparent to the light beams which are emitted by the LED and has a refractive index which is significantly larger, the light which is emitted by the LED is refracted to an adequate extent in the direction of the middle axis of the light transmission part.

The lateral surface of the first section of the light transmission part is preferably polished and at the outer side is surrounded by a gaseous medium. This design is based on the fact that the conditions for a total reflection are fulfilled at the lateral surface of the first section if the first section of the light transmission part, as already mentioned, is formed from a material such as glass, crystal or of a plastic which is transparent to the light beams which are emitted by the LED, with a refractive index of n=1.4 or larger and the refractive index of the medium which surrounds the first section, such as air or another gaseous medium, is about n=1. Herein, the purpose of the polishing of the lateral surface is hereby for the light beams which are incident upon the lateral surface to be reflected at the lateral surface in a directed manner. Due to the comparatively large refractive index jump between the medium which surrounds the first section of the light transmission part and the material of the first section of the light transmission part and due to the polishing of the lateral surface, essentially all light beams which enter from the LED into the first section of the light transmission part are refracted comparatively heavily in the direction of the middle axis of the light transmission part and completely reflected at the lateral surface of the first section of the light transmission part.

The first section of the light transmission part can advantageously be surrounded by a sleeve, in order to prevent an undesirable, time-related and/or environment-related or application-related change of the lateral surface of the first section of the light transmission part, caused for example by the accumulation or deposits of substances, wherein this sleeve is usefully arranged distanced to the lateral surface of the first section and shields the first section of the light transmission part from its outer environment.

If for example one wishes to do without the aforementioned surrounding sleeve, then it can be advantageous for the lateral surface of the first section of the light transmission part to be polished, wherein a layer which is highly reflective to the radiation which is emitted by the LED is provided at the outer side of the lateral surface. The highly reflective layer which on using an LED which emits white light can consist for example of silver or aluminum, forms a mirror surface and here serves for the reflection of all light beams which are incident upon the lateral surface of the first section. Here too, the polishing of the lateral surface has the purpose of the light beams which are incident upon the lateral surface being reflected at the lateral surface in a directed manner. The use of a highly reflective layer on the lateral surface of the first section of the light transmission part furthermore has the further advantage that deposits on the lateral surface are of no significance with regard to the manner of functioning of the first section of the light transmission part as long as they do not change or damage the highly reflective layer. A sleeve which surrounds the first section of the light transmission part at the outer side is therefore not necessary.

Alternatively to a design, with regard to which the first section of the light transmission part is designed homogeneously of one material, wherein the lateral surface of the first section possibly comprises a highly reflective coating, the first section of the light transmission part can also be formed by a fiber truncated cone, wherein the fibers of the fiber truncated cone consist of a core-cladding glass. However, with regard to this design, it is to be ensured that the individual fibers have such a large numeric aperture that even those light beams which are emitted by the LED into the fiber truncated cone and which are aligned at a very large angle relative to the middle axis of the light transmission part are reflected at the transitions of the core glass to the cladding glass of the individual fibers and are transformed into light beams with a smaller angle relative to the middle axis of the light transmission part.

The second section of the light transmission part can likewise be advantageously formed from a core-cladding glass. This means that the second section of the light transmission part can comprise a rod-like core of a core glass which at its outer periphery is encased by a glass, the cladding glass, which is different to the core glass with regard to the refractive index. The core glass and the cladding glass of the second section of the light transmission part usefully correspond to the core glass and the cladding glass which are used in the fiber-optic or they have a refractive index jump which corresponds essentially to the refractive index jump between the refractive index of the core glass which is used in the fiber-optic and the refractive index of the cladding glass which is used in the fiber-optic. The refractive index jump between the core glass and the cladding glass which are used in the second section of the light transmission part defines which light beams are transmitted further to the fiber-optic on account of the total refection and which light beams already leave the second section of the light transmission part at its lateral surface due to the requirements for a total reflection no longer being fulfilled.

With regard to a second section of the light transmission part which is formed from a core-cladding glass and given an adequately large length of the second section in the direction of the middle axis of the light transmission part, light beams whose angle is large enough with respect to the middle axis of the light transmission part leave the core glass of the second section and penetrate into its cladding glass, since the conditions for a total reflection are no longer fulfilled at the transition of the core glass to the cladding glass. In particular, if the cladding glass is surrounded at the outer side by a gaseous medium with a refractive index of about n=1 and the cladding glass comprises a smooth outer lateral surface, then the comparatively large refractive index jump between the refractive index of the cladding glass and the refractive index of the gaseous medium can result in a total reflection of the light beams which have penetrated into the cladding glass taking place at the interface between the cladding glass and its outer environment. The light beams which have penetrated into the cladding glass are then led further within the cladding glass to the fiber-optic, which is not desirable. In order to prevent this from happening, one preferably envisages the outer lateral surface of the cladding glass being roughened. At the latest, the light beams which have penetrated into the cladding glass leave the cladding glass after a few reflections at the interface between the cladding glass and its outer environment and via the outer lateral surface get into the outer environment (surroundings) of the second section of the light transmission part.

Instead of a second section of the light transmission part which is formed from a core-cladding glass, the second section of the light transmission part can advantageously also be formed merely from a material which is transparent to the light beams which are emitted by the LED, wherein the second section is then surrounded at its lateral surface by a material, whose refractive index differs from the refractive index of the material of the second section of the light transmission part. In order, with regard to this design, to be able to eliminate light beams with a large angle relative to the middle axis of the light transmission part in the second section of the light transmission part, the material of the second section and the material which surrounds this section at the outer periphery is usefully selected such that the material of the second section and the material which surrounds this section produce the same refractive index jump as the core-cladding glass of the fiber optic. The second section of the light transmission part can be formed for example of pure core glass. Concerning the material which surrounds the second section, this can be an adhesive which can also be used to fix the second section and preferably the complete light transmission part in an assembly environment. Further, under certain circumstances, it can also be advantageous for the material which surrounds the second section to be designed transparently to the light beams which are emitted by the LED. Practically no radiation which would otherwise possibly accelerate the ageing of this material is absorbed by this material due to its transparency. In particular, this can be of significance if the material which surrounds the second section of the light transmission part is a plastic such as for example an adhesive and high radiation powers are to be transmitted in the illumination device.

According to a further preferred further development of the invention, the second section of the light transmission part is preferably surrounded by a component which is designed for receiving the radiation which is emitted by the LED. Accordingly, the component which surrounds the second section and which is usefully a sleeve is advantageously designed in a manner such that it has a large absorption capacity for the light beams which are emitted by the LED and advantageously also has a high thermal conductivity. The component can be designed for example of metal and at its side which faces the second section of the light transmission part can be non-conductively surface-coated for example with an anodized layer. Furthermore, the component can be connected to the second section of the light transmission part via an adhesive which completely surrounds the lateral surface of the second section. Herein, it has been found to be favorable for the adhesive to comprise a high transparency to the light beams which are emitted by the LED. If the second section is formed by a core-cladding glass, it is further useful for the refractive index of the transparent adhesive to correspond as much as possible to the refractive index of the cladding glass of the core-cladding glass.

As an alternative to a design, concerning which the second section of the light transmission part is formed by a rod-like component of a core-cladding glass, the second section of the light transmission part can also be formed by a fiber bundle, wherein the fibers of the fiber bundle each consist of a core-cladding glass. Herein, the refractive index jump between the core glass and the cladding glass of the individual fibers of the second section is ideally essentially equal to the refractive index jump between the core glass and the cladding glass of the fiber optic. One advantage of a second section of the light transmission part which is formed by a fiber bundle lies in the fact that the cross section of the second section can be comparatively simply adapted to the cross section of a fiber-optic which likewise consists of a fiber bundle.

In the simplest case, the light transmission part is advantageously formed by one component. A rod of core-cladding glass whose cross section corresponds essentially to the cross section of the fiber-optic can therefore serve as a base part for the light transmission part. For manufacturing the light transmission part from the base part, the cladding glass and also a part of the core glass is removed at a region of the base part which is adjacent to an end of the base part, in a manner such that the cross section of the base part tapers departing from the region, at which the base part still comprises the cladding glass.

Instead of a single-part design of the transmission part, according to the invention one also envisages the light transmission part being formed from two separate components. In this case, one component forms the first section of the light transmission part which directly faces the LED and which comprises cross section widening with an increasing distance to the LED as well as a lateral surface which in an angularly independent manner reflects the radiation which enters into the first section, and a second component forms the second section of the light transmission part which directly faces the fiber-optic and which comprises at least one lateral surface which in an angularly dependent manner reflects radiation which enters from the first section into the second section. The two components which form the light transmission part can be arranged loosely next to one another or be connected to one another. However, at all events it is to be ensured that the two components are positioned as close as possible to one another, in order to minimize transmission losses with the transmission of light beams from the first component to the second component. With regard to such transmission losses, concerning an embodiment with which the two components are connected to one another, it is useful if an adequately temperature-resistant optical adhesive is used for connecting the two composites, wherein the applied adhesive particularly preferably has a refractive index which largely corresponds to the refractive index of the materials of the two components which serve for transporting the light beams which are emitted by the LED, to the fiber-optic.

It has already been stated that the cross section of the first section of the light transmission part on the one hand should be designed large enough, in order to be able to receive a maximum of light beams which are emitted by the LED and on the other hand should be kept as small as possible, in order to achieve an as favorable as possible aspect ratio. In this context, one advantageously envisages the cross-sectional profile of the first section of the light transmission part at the end of the first section which faces the LED corresponding to the profile of the light-emitting surface of the LED in the lateral direction. This means that the cross section of the first section of the light transmission part, with regard to its size and shape preferably essentially corresponds to the light-emitting surface of the LED in the lateral direction. Since the light-emitting surfaces of LED chips are mostly designed in a rectangular or square manner, the cross section of the first section of the light transmission part preferably at its end which faces the LED also has a rectangular or square cross section with the dimensions of the light-emitting surface of the LED. If the light-emitting surface of the LED has a round cross section, then the cross section of the first section of the light transmission part at its end which faces the LED also has a correspondingly dimensioned round cross section.

With applications, concerning which it is not necessary to remove the fiber-optic from the illumination device according to the invention, it has been found to be advantageous if the light transmission part is connected to the fiber-optic by way of a temperature-resistant material connection. In this context, a temperature-resistant optical adhesive is applied between the second section of the light transmission part and the fiber-optic, for the material connection of the light transmission part to the fiber-optic, wherein concerning the transmission efficiency from the light transmission part to the fiber-optic, it is useful if the applied adhesive has a refractive index which largely corresponds to the refractive index of the materials of the two components which serve for transporting the light beams which are emitted by the LED, from the light transmission part to the fiber-optic.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
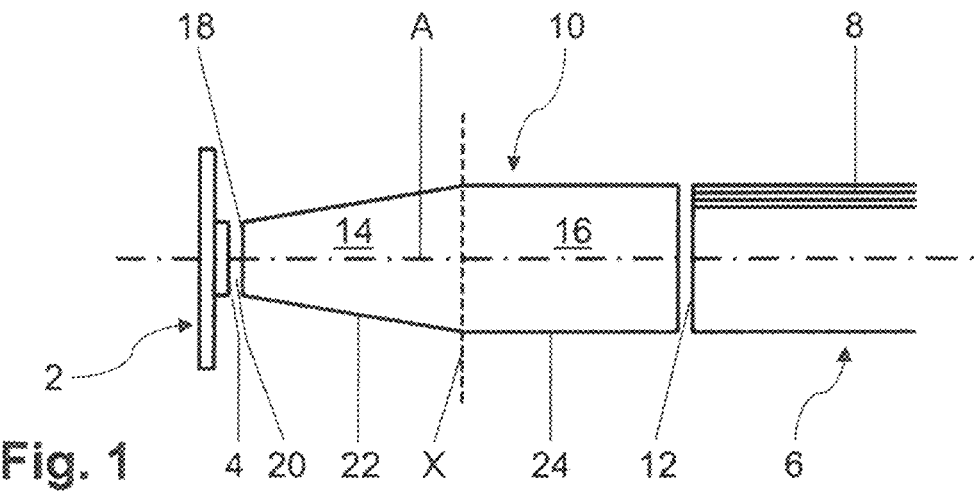
FIG. 1 is a lateral view showing an illumination device with a light transmission part.

Referring to the drawings, the illumination device which is represented in FIG. 1, apart from an LED 2 with a light-emitting surface 4 comprises a fiber-optic 6, into which the light which is emitted by the LED 2 is coupled. The fiber-optic 6 consists of a multitude of light-conductive fibers 8 which each consist of a core-cladding glass. The cross section of an end-face 12 of the fiber-optic 6 which faces the LED 2 is larger than the cross section of the light-emitting surface 4 of the LED 2. The coupling of the light beams which are emitted by the LED 2, into the fiber-optic 6, is not effected in a direct manner but via a light transmission part 10 which is arranged between the LED 2 and the fiber-optic 6 and which consists of a material with a refractive index n>1.4 which is transparent to the radiation which is emitted by the LED 2.

As is rendered recognizable in the drawing by the dashed line X, the light transmission part 10 comprises two sections 14 and 16. Of these two sections 14 and 16, a first section 14 directly faces the LED 2 and a second section 16 directly faces the fiber-optic 6. The outer shape of the second section 16 of the light transmission part 10 is cylindrical, wherein the cross section of the second section 16 corresponds to the cross section of the end-face 12 of the fiber-optic 2.

Departing from the cross section of the second section 16, the cross section of the first section 14 of the light transmission part 10 continuously reduces with a decreasing distance to the LED 2. An end-face 18 which lies directly opposite the light emitting surface 4 of the LED 2 therefore has a smaller cross section than an end-face which is located at the dashed line X. The cross section of the end-face 18 of the first section 14 of the light transmission part 10 corresponds at least to the cross section of the light-emitting surface 4 of the LED 2, in order to be able to receive as much as possible of the radiation which is emitted by the LED 2, wherein the distance between the end-face 18 of the first section 14 of the transmission part 10 and the light-emitting surface 4 of the LED 2 is very low. Air, which in the embodiment example which is represented in FIG. 1 also surrounds the complete light transmission part 10 at the outer side and has a refractive index of n=1 is located in an intermediate space 20 between the end-face 18 and the light-emitting surface 4.

A part of the light beams which are emitted by the LED 2 has a comparatively large angle to a middle axis A of the light transmission part 10. These light beams, in the first section 14 of the light transmission part 10 are incident upon an outer, polished lateral surface 22 of the section 14. The radiation which is incident upon the lateral surface 22 of the section 14 is reflected in a total manner at the lateral surface 22 independently of its angle to the lateral surface 22 on account of the comparatively large refractive index jump between the material, from which the section 14 of the light transmission part 10 consists, and the air which surrounds the section 14. The shaping of the first section 14 of the light transmission part 10 with the cross section which continuously enlarges in the direction of the second section 16 of the light transmission part 10 herein has the effect that the beams which are reflected by the lateral surface 22 have an angle relative to the middle axis A of the light transmission part 10 which is smaller than that which they had on entry into the first section 14 of the light transmission part 10.

Despite this angular transformation, a few light beams with such a large angle with respect to the middle axis A of the illumination device 10 that these light beams cannot be transmitted up to the end of the fiber-optic 6 which is away from the light transmission part 10 on account of the comparatively low numeric aperture of the light-conductive fibers 8 of the fiber-optic can still yet be present at the exit side of the first section 14 of the light transmission part 10. These light beams are eliminated in the second section 16 of the light transmission part 10. For this purpose, with the embodiment example which is represented in FIG. 1, the second section 16 of the light transmission part 10 has an outer lateral surface 24, at which only those light beams are reflected which are incident thereupon and which can be transmitted from the fiber-optic 6 due to the restricted numerical aperture of the light-conductive fibers 8 of the fiber-optic 6. The remaining light beams which have a large angle relative to the middle axis A of the light transmission part 10 and cannot be transmitted by the fiber-optic 6 leave the second section 16 of the light transmission part 10 via its lateral surface 24.

Figure 2:
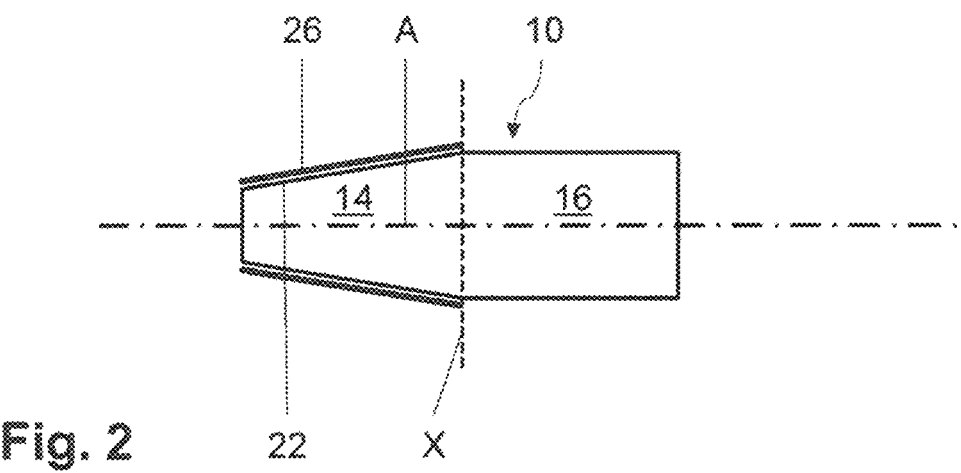
FIG. 2 is a lateral view showing a light transmission part according to a second embodiment.

The light transmission part 10 which is represented in FIG. 2 differs from the light transmission part 10 which is shown in FIG. 1 with regard to the design of the first section of the light transmission part 10. Here, a highly reflective layer 26 is deposited onto the outer side of the outer lateral surface 22 of the first section 14. This layer 26 therefore forms a mirror surface, at which all light beams which are incident upon the lateral surface 22 of the first section 14 are reflected.

Figure 3:
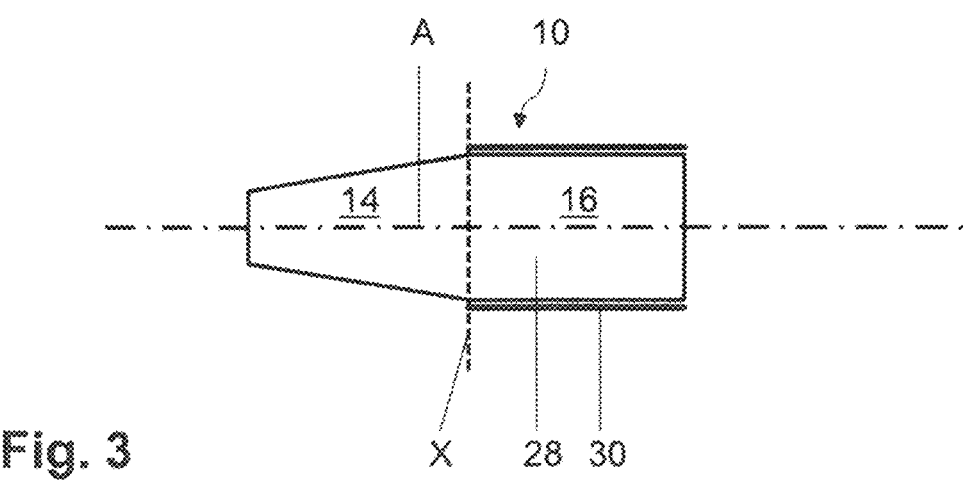
FIG. 3 is a lateral view of a light transmission part according to a third embodiment.
Figure 4:
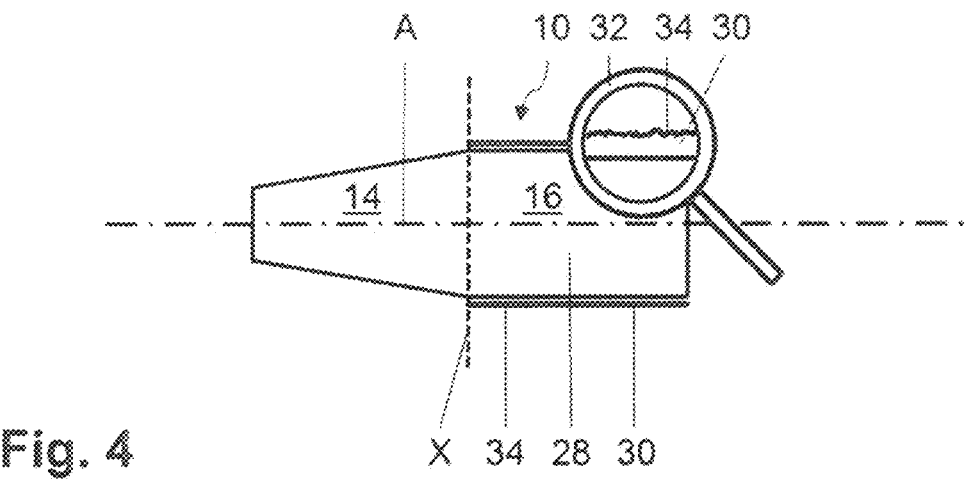
FIG. 4 is a lateral view of the light transmission part according to FIG. 3.

A light transmission part 10 whose second section 16 is formed from a core-cladding glass is represented in FIGS. 3 and 4. Herein, the second section 16 comprises a core 28 of a core glass. At the outer periphery, a cladding 30 of a cladding glass which forms the outer peripheral surface 34 of the second section 16 connects onto the core 28 at the outer periphery. The applied core glass and cladding glass of the second section 16 correspond to the core glass and cladding glass which is used with a fiber-optic 6 which is applied in combination with the light transmission part 10.

A region of the cladding 30 of the second section 16 of the light transmission part 10 is represented in an enlarged manner in FIG. 4 and is rendered recognizable by a magnification 32. It can be derived from the region which is encompassed by the magnification 32 that the outer lateral surface 34 of the cladding of cladding glass 30 is roughened. A total reflection of the light beams which have penetrated the cladding 30 is to be prevented by way of this.

Figure 5:
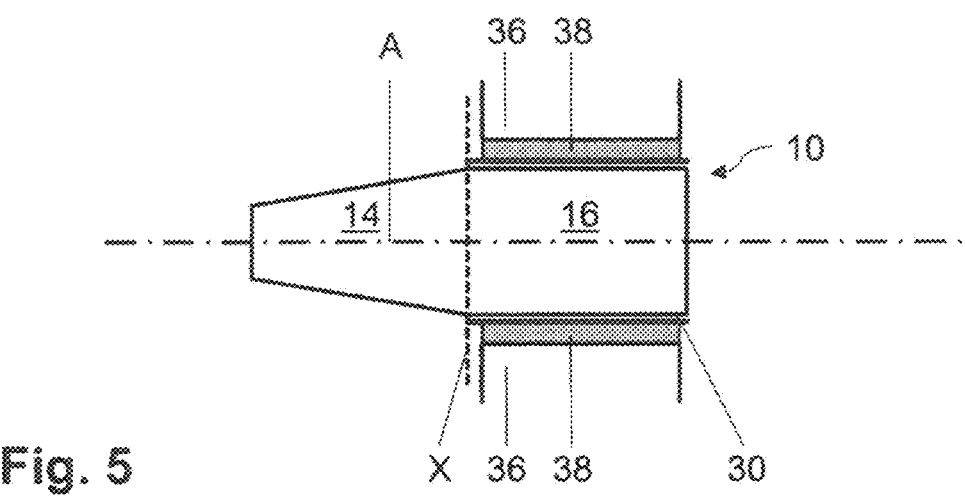
FIG. 5 is a lateral view of a light transmission part according to a fourth embodiment.

A design, concerning which the second section 16 of the light transmission part 10 is surrounded by a component 36 can be derived from FIG. 5. The second section 16 is shown in FIG. 5 by way of example as core-cladding glass with a core 28 and with a cladding 30. The component 36 which can be a holder for the light transmission part 10 is formed from metal and on account of its surface nature due to it having been anodized for example has a high absorption capacity for the light beams which are emitted by the LED 2 and has a high thermal conductivity. The component 36 is materially connected to the second section 16 of the light transmission part 10 via a layer of plastic 38 which is deposited on the outer side of the cladding 30. This adhesive 38 has a high transparency to the light beams which are emitted by the LED 2 and has a high refractive index which corresponds largely to the refractive index of the cladding glass of the core-cladding glass.

Figure 6:
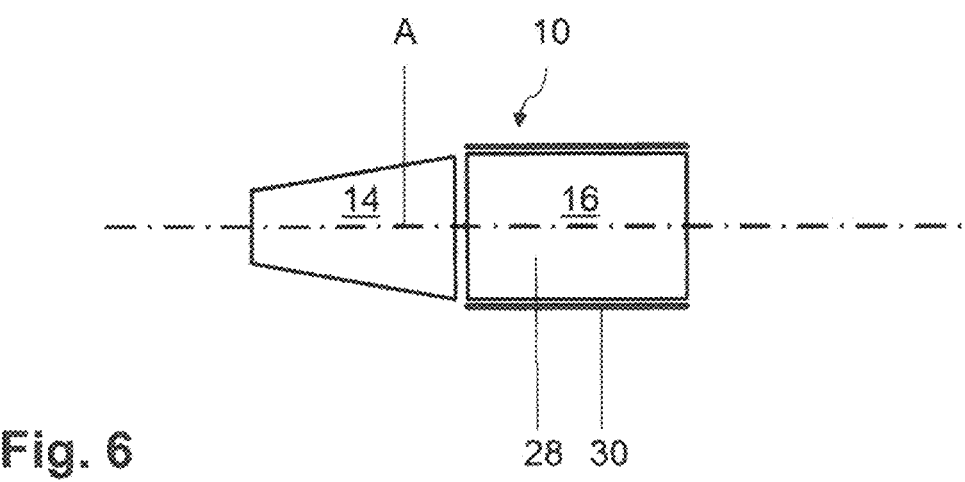
FIG. 6 is a lateral view of a light transmission part according to a fifth embodiment.
Figure 7:
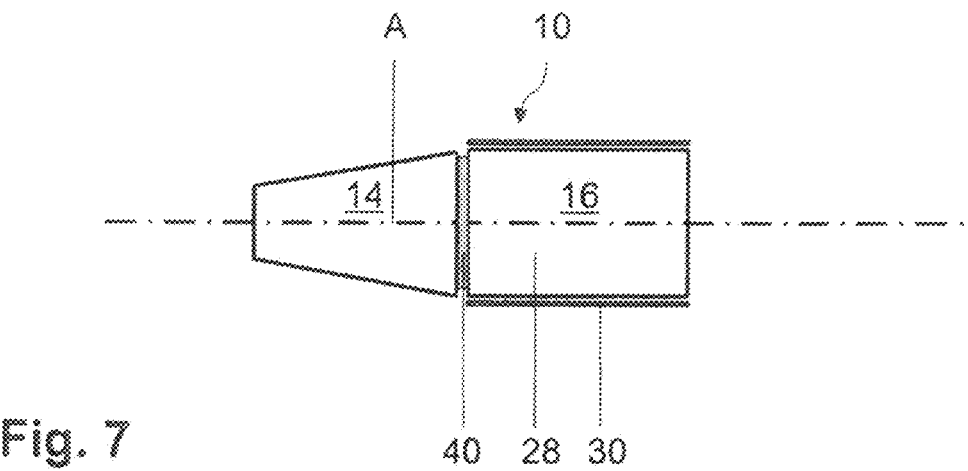
FIG. 7 is a lateral view of a light transmission part according to a sixth embodiment.
Figure 8:
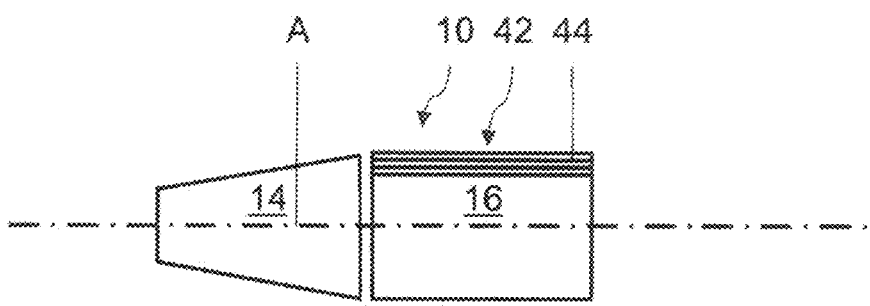
FIG. 8 is a lateral view of a light transmission part according to a seventh embodiment.

Whereas the light transmission parts 10 which are represented in the FIGS. 1-5 are designed as one part, the light transmission parts 10 which are represented in FIG. 6-8 are designed in a two-part manner. Here, the first section 14 and the second section 16 of the light transmission part 10 are each formed by separate components. In contrast to the light transmission parts 10 which are represented in FIGS. 6 and 8 and with regard to which the two components forming the first section 14 and the second section 16 are arranged loosely next to one another, with regard to the light transmission part 10 which is represented in FIG. 7 the component which forms the first section 14 of the light transmission part 10 is materially connected to the second section 16 of the light transmission part 10. For this, a layer of a temperature-resistant optical adhesive 40 is arranged between the component which forms the first section 14 and the component which forms the second section 16. The applied adhesive 40 has a refractive index which corresponds essentially to the refractive indices of the two sections 14 and 16 of the light transmission part 10.

The light transmission part 10 which is represented in FIG. 8 differs from the light transmission part 10 which is represented in FIG. 6 merely with regard to the design of the second section 16 of the light transmission part 10. In contrast to the light transmission part 10 which is shown in FIG. 6 and with regard to which the second section 16 is formed from a core-cladding glass with a core 28 and a cladding 30, the second section 16 of the light transmission part 10 which is represented in FIG. 8 is formed by a fiber bundle 42 of with a plurality of fibers 44 of core-cladding glass. The refractive index jump between the core glass and the cladding glass of the individual fibers 44 is hereby equal to the refractive index jump between the core glass and the cladding glass of the fibers 8 of the fiber-optic 6.

Figure 9:
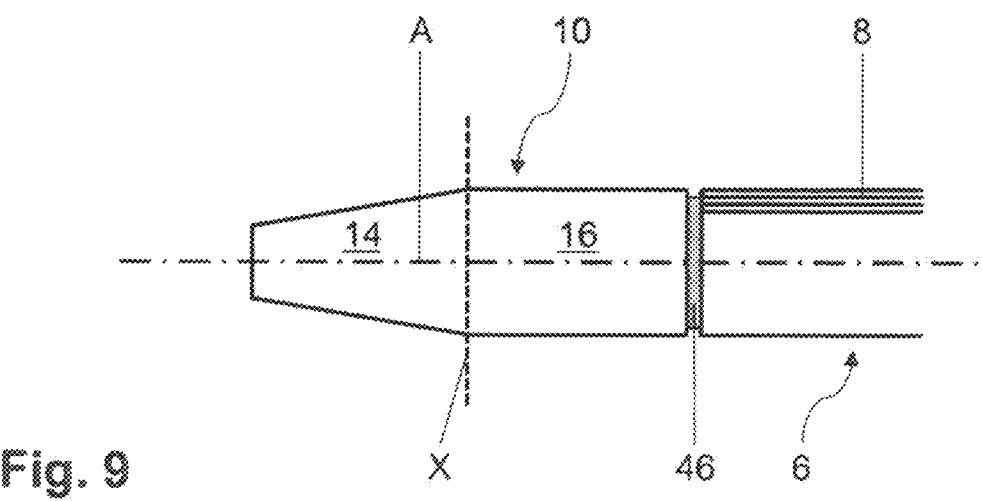
FIG. 9 is a lateral view of a light transmission part and a fiber-optic.

It is to be derived from FIG. 9 that the light transmission part 10 can be materially connected to the fiber-optic 6. This connection is effected by a layer of adhesive 46 which is arranged between the light transmission part 10 and the fiber-optic 6. The applied plastic 46 is transparent to the light beams which are emitted by the LED 2 as well as temperature-resistant and has a refractive index which corresponds to the refractive index of the fibers 8 of the fiber-optic 6 and the refractive index of the material of the section 16 which serves for leading the light beams further from the LED 2 into the fiber-optic 6.

Figure 10:
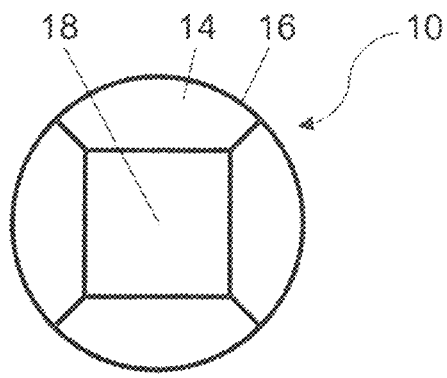
FIG. 10 is a lateral view of a light transmission part according to an eighth embodiment.
Figure 11:
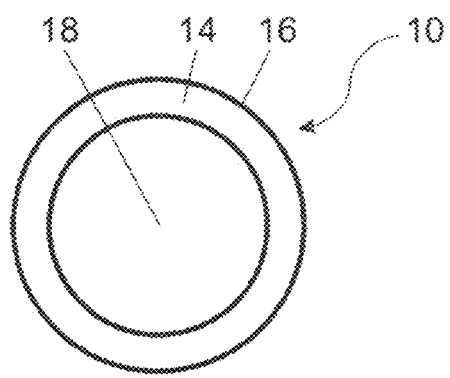
FIG. 11 is a lateral view of a light transmission part according to a ninth embodiment.

The cross section of the first section 14 of the light transmission part 10, at its end which faces the LED 2 and with regard to its shape and dimensions corresponds to the cross section of the light-emitting surface 4 of the LED 2. This is particularly clear from FIGS. 10 and 11. If the LED 2 has a rectangular, light-emitting surface 4, then, as is shown in FIG. 10, the end-face 18 of the first section 14 of the light transmission part 10 is likewise designed in a rectangular manner with the dimensions of the light-emitting surface 4 of the LED 2. In this case, the first section 14 has a shape similar to a truncated pyramid. If the cross section of the light-emitting surface 4 of the LED 2 is round, then the end-face 18 of the first section 14 of the light transmission part 10 is likewise round with a the diameter of the light-emitting surface 4 of the LED 2. In this case, the first section 14 of the light transmission part is designed in the shape of a truncated cone. This is evident from FIG. 11.

Figure 12:
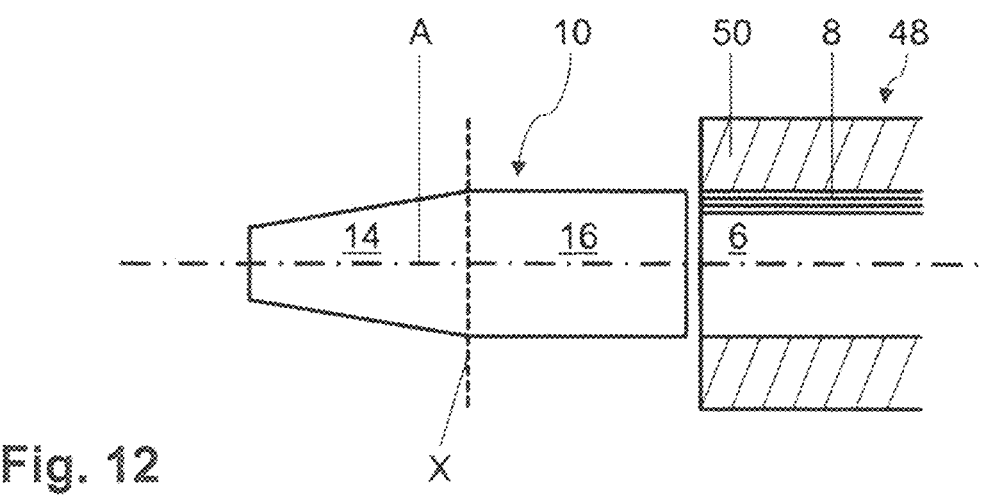
FIG. 12 is a lateral view of a light transmission part and a fiber-optic cable.

Finally, FIG. 12 shows that a fiber-optic 6 which consists of a multitude of light-conducting fibers 8 can be part of a fiber-optic cable 48 and in this case is arranged in a sleeve 50. The sleeve 50 can be e.g. a metal sleeve.

While specific embodiments of the invention have been shown and described in detail to illustrate the application of the principles of the invention, it will be understood that the invention may be embodied otherwise without departing from such principles.

The invention claimed is:

1. An illumination device, comprising:
    an LED;
    a fiber-optic; and
    a light transmission part arranged between the LED and the fiber-optic and comprising:
        a first section directly facing the LED and comprising a cross section which widens with an increasing distance to the LED as well comprising a lateral surface independently angularly reflecting radiation which enters into the first section; and
        a second section directly facing the fiber optic and comprising at least one lateral surface dependently reflects radiation angularly, the radiation entering the first section into the second section, the second section comprising a core, wherein a refractive jump between the core and an outer periphery of the second section corresponds to a refractive index jump of the fiber optic.

2. An illumination device according to claim 1, wherein the light transmission part is arranged distanced to the LED and an intermediate space between the LED and the light transmission part is gas-filled.

3. An illumination device according to claim 1, wherein the lateral surface of the first section of the light transmission part is polished and at an outer side of the first section of the light transmission part is surrounded by a gaseous medium.

4. An illumination device according to claim 1, wherein:
    the lateral surface of the first section of the light transmission part is polished; and
    a layer, which is highly reflective to the radiation which is emitted by the LED, is provided at the outer side of the lateral surface.

5. An illumination device according to claim 1, wherein the first section of the light transmission part is formed by a fiber truncated cone, the fiber truncated cone comprising fibers consisting of a core-cladding glass.

6. An illumination device according to claim 1, wherein the second section of the light transmission part is formed from a core-cladding glass.

7. An illumination device according to claim 6, wherein an outer lateral surface of the core-cladding glass is roughened.

8. An illumination device according to claim 1, wherein the second section of the light transmission part is formed from a material which is transparent to the radiation emitted by the LED and at the lateral surface is surrounded by a material with a refractive index which differs from a refractive index of the material of the second section of the light transmission part.

9. An illumination device according to claim 1, further comprising a surrounding component, wherein the second section of the light transmission part is surrounded by the surrounding component and the surrounding component is configured for receiving the radiation which is emitted by the LED.

10. An illumination device according to claim 1, wherein the second section of the light transmission part is formed by a fiber bundle, wherein fibers of the fiber bundle each consist of core-cladding glass.

11. An illumination device according to claim 1, wherein the light transmission part is formed from one component.

12. An illumination device according to claim 1, wherein the light transmission part is formed by two separate components.

13. An illumination device according to claim 1, wherein a cross-sectional profile of the first section of the light transmission part, at the end of the first section which faces the LED corresponds to the profile of the light-emitting surface of the LED in the lateral direction.

14. An illumination device according to claim 1, further comprising a temperature-resistant material connection, wherein the light transmission part is connected to the fiber-optic by way of the temperature-resistant material connection.

15. An illumination device according to claim 1, wherein the core comprises a rod core of glass, the rod core of glass having an outer core periphery, the outer core periphery being encased by another glass, the another glass having another glass refractive index, the rod core of glass having a rod core refractive index, the rod core refractive index being different from the another glass refractive index.

16. An illumination device according to claim 1, wherein the second section has a constant cross-section over a complete length of the second section in a direction of a middle axis of the light transmission part, the light transmission part being located at a spaced location from the fiber-optic.

17. An illumination device, comprising:
   an LED;
   a fiber-optic comprising a first refractive index jump; and
   a light transmission part arranged between the LED and the fiber-optic and comprising:
      a first section directly facing the LED and comprising a cross section which widens with an increasing distance to the LED as well comprising a lateral surface independently reflecting radiation which enters into the first section; and
      a second section directly facing the fiber optic and comprising at least one lateral surface dependently reflects radiation entering from the first section into the second section, the second section comprising a core and a second section outer periphery, wherein a second refractive index jump between the core and the second section outer periphery is equal to the first refractive index jump.

18. An illumination device according to claim 17, wherein the core comprises a rod core of glass, the rod core of glass having an outer core periphery, the outer core periphery being encased by another glass, the another glass having another glass refractive index, the rod core of glass having a rod core refractive index, the rod core refractive index being different from the another glass refractive index.

19. An illumination device according to claim 17, wherein the second section has a constant cross-section over a complete length of the second section in a direction of a middle axis of the light transmission part, the light transmission part being located at a spaced location from the fiber-optic.

20. An illumination device according to claim 19, wherein the cross-section of the second section has a dimension equal to a dimension of a cross-section of the fiber optic.

* * * * *